(12) United States Patent  
Compton

(10) Patent No.: US 9,175,960 B1  
(45) Date of Patent: Nov. 3, 2015

(54) OPTICALLY DITHERED ATOMIC GYRO-COMPASS

(71) Applicant: Honeywell International Inc., Morristown, NJ (US)

(72) Inventor: Robert Compton, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 14/482,826

(22) Filed: Sep. 10, 2014

(51) Int. Cl.
*G01N 21/00* (2006.01)
*G01C 19/58* (2006.01)
*G01C 17/00* (2006.01)
*G01N 21/68* (2006.01)
*G01N 21/64* (2006.01)
*H01J 37/32* (2006.01)

(52) U.S. Cl.
CPC ........... *G01C 19/58* (2013.01); *G01C 17/00* (2013.01); *G01N 21/64* (2013.01); *G01N 21/68* (2013.01); *H01J 37/32935* (2013.01)

(58) Field of Classification Search
CPC ... H01J 37/32935; G01N 21/64; G01N 21/68; G01N 2015/1037; G01J 3/02
USPC ...................... 356/72–73, 300–445
See application file for complete search history.

(56) References Cited

U.S. PATENT DOCUMENTS 5,528,028 A * 6/1996 Chu .................. H05H 3/04 250/251
7,359,059 B2    4/2008 Lust et al.
2013/0213135 A1   8/2013 Compton et al.
2014/0016118 A1   1/2014 Compton et al.
2014/0022534 A1   1/2014 Strabley et al.
2014/0061454 A1   3/2014 Loftus et al.

OTHER PUBLICATIONS

Cameron, "Get Back, Loretta: DARPA Seeks to Eliminate GPS Dependence", "http://gpsworld.com/get-back-loretta-darpa-seek-to-eliminate-gps-dependence", Jul. 24, 2013, pp. 3-6, Publisher: GPS World Magazine, Published in: US.
Gustavson, "Cold Atom Gyros", "IEEE Sensors 2013 Tutorial: Cold Atom Gyros", Nov. 3, 2013, pp. 1-82, Publisher: IEEE, Published in: US.
Gustavson et al., "Rotation Sensing With a Dual Atom-Interferometer SAGNAC Gyroscope", Mar. 24, 2000, pp. 2385-2398, Publisher: Physics Department, Yale University, Published in: US.
Kasevich, "Cold Atom Navigation Sensors", Nov. 19, 2007, pp. 1-29, Publisher: Stanford University, Published in: US.

(Continued)

*Primary Examiner* — Abdullahi Nur
(74) *Attorney, Agent, or Firm* — Fogg & Powers LLC

(57) ABSTRACT

Systems and methods for an optically dithered atomic gyro-compass are provided. In one embodiment, an inertial sensor comprises: a vacuum chamber containing a cloud of laser cooled alkali atoms, wherein the atoms are free to fall under the influence of gravity; a first set of laser sources applying a first set of laser beams into the cloud along a first axis; a second set of laser sources applying a second set of laser beams into the cloud along a second axis; wherein the first set and second sets of laser beams apply coherent laser pulses that separate a wave function of the atoms along trajectories defining a plane sensitive to rotation about an axis orthogonal to the plane; and wherein the first and second set of laser sources apply dithering to the axis by modulating a relative magnitude of the first laser beams with respect to the second laser beams.

20 Claims, 8 Drawing Sheets

(56) References Cited

OTHER PUBLICATIONS

Keller, "AOSense to Develop Navigation Chip That Combines Solid-State and Atomic Inertial Sensors", "http://www.militaryaerospace.com/articles/2013/AOSense-DARPA-CSCAN.html", Apr. 11, 2013, pp. 1-12, Publisher: Military Aerospace, Published in: US.

Landragin et al., "Atomic Gyroscope: Present Status and Prospective", Nov. 18, 2009, pp. 1-42, Publisher: SYRTE—Observatoire de Paris, Published in: Paris, France.

Vancamp et al., "Towards a High-Precision Atomic Gyroscope", May 30, 2013, pp. 1-72, Publisher: Massachusettes Institute of Technology, Published in: US.

* cited by examiner

OPTICALLY DITHERED ATOMIC GYRO-COMPASS

BACKGROUND

Northfinding gyro-compasses operate by using gyroscopes to measure the Earth's rate of rotation. Since the Earth's rate of rotation is both a constant and known value, the perceived rate of rotation measured by a gyroscope can be used to determine the amount of angular misalignment between the gyroscopes sensing axis and the axis around which the Earth spins. If a triad of three orthogonally oriented gyroscopes is utilized, each will measure a projection of the Earth's rotation onto the sensing axis of that gyroscope. By utilizing these three projections, the northfinding compass can indicate which direction is north. Gyroscopes typically exhibit some quantity of bias error. That is, they will measure some rate of rotation even when there is no rotation occurring. Gyroscopes that are both accurate and stable (and thus inherently experience relatively little bias error) tend to be large, heavy, and consume large quantities of power. Therefore, they are not well suited for use with miniature, dismounted gyrocompasses that are desirable for applications such as remote targeting applications.

Microelectrical-mechanical (MEMS) gyroscopes represent one technology for producing small, lightweight and low power consuming gyroscope. A good accelerometer may be used in conjunction with the gyroscope, elimination one degree of freedom by pointing the gyroscope's sense axis towards the Earth's center. Dithering techniques have also been developed to mitigate bias error in these MEMS devices and address the other degree of freedom. That is, the MEMS gyroscopes are mechanically oscillated at a set modulation frequency along their sensing axis with respect to the estimated direction of North. This motion results in the MEMS gyroscope producing a rotation rate output signal that is modulated in time. By demodulating that signal, the bias error is removed and a measurement of the Earth's rotation rate can be obtained. However, implementation of this dithering involves mounting each MEMS gyroscope on a platform that includes rotating stages. Thus mechanical dithering of the MEMS gyroscopes introduces additional moving parts that are subject to wear-and-tear, mechanical failure, and varying performance characteristics over time.

For the reasons stated above and for other reasons stated below which will become apparent to those skilled in the art upon reading and understanding the specification, there is a need in the art for improved systems and methods for optically dithered atomic gyro-compasses.

SUMMARY

The Embodiments of the present invention provide methods and systems for optically dithered atomic gyro-compasses and will be understood by reading and studying the following specification.

Systems and methods for an optically dithered atomic gyro-compass are provided. In one embodiment an optically dithered atomic inertial sensor comprises: a vacuum chamber containing an atom cloud of laser cooled alkali atoms, wherein the alkali atoms are free to fall under the influence of gravity; a first set of laser sources configured to apply a first set of laser beams into the atom cloud along a first axis; a second set of laser sources configured to apply a second set of laser beams into the atom cloud along a second axis; wherein the first set of laser beams and the second set of laser beams apply a series of coherent laser pulses into the atom cloud that separate a quantum-mechanical wave function of the alkali atoms along trajectories that define a sensing plane that is sensitive to rotation about a sensing axis oriented orthogonal to the sensing plane; and wherein the first set of laser sources and the second set of laser sources apply a dithering motion to the sensing axis by modulating a relative magnitude of the first set of laser beams with respect to the second set of laser beams.

DRAWINGS

Embodiments of the present invention can be more easily understood and further advantages and uses thereof more readily apparent, when considered in view of the description of the preferred embodiments and the following figures in which:

FIG. 1 is a diagram illustrating an optically dithered atomic inertial sensor of one embodiment of the present disclosure;

FIG. 2 a diagram illustrating a rotation sense axis defined by the separation of a quantum-mechanical wave function of for one embodiment of the present disclosure;

In accordance with common practice, the various described features are not drawn to scale but are drawn to emphasize features relevant to the present invention. Reference characters denote like elements throughout figures and text.

DETAILED DESCRIPTION

In the following detailed description, reference is made to the accompanying drawings that form a part hereof, and in which is shown by way of specific illustrative embodiments in which the invention may be practiced. These embodiments are described in sufficient detail to enable those skilled in the art to practice the invention, and it is to be understood that other embodiments may be utilized and that logical, mechanical and electrical changes may be made without departing from the scope of the present invention. The following detailed description is, therefore, not to be taken in a limiting sense.

Embodiments of the present disclosure address the need for miniaturized accurate and stable gyroscopes, for applications such as gyrocompassing, by disclosing dithering techniques for atomic sensor gyroscope. That is, the present disclosure provides systems and methods for rotating the optics within an atomic gyroscope in a virtual sense by electrically turning the vector in which light is applied to atoms within the gyroscope. The resulting effect to the output signal of the gyroscope is identical to what would be obtained through mechanical dithering. The input axis of the gyroscope is modulated, producing a rotation rate output signal that is modulated in time. By demodulating that signal, bias error is removed and a measurement of the Earth's rotation along the sensing axis rate can be obtained. As detailed below, the dithering is achieved without introducing the need for moving parts.

Figure 1:
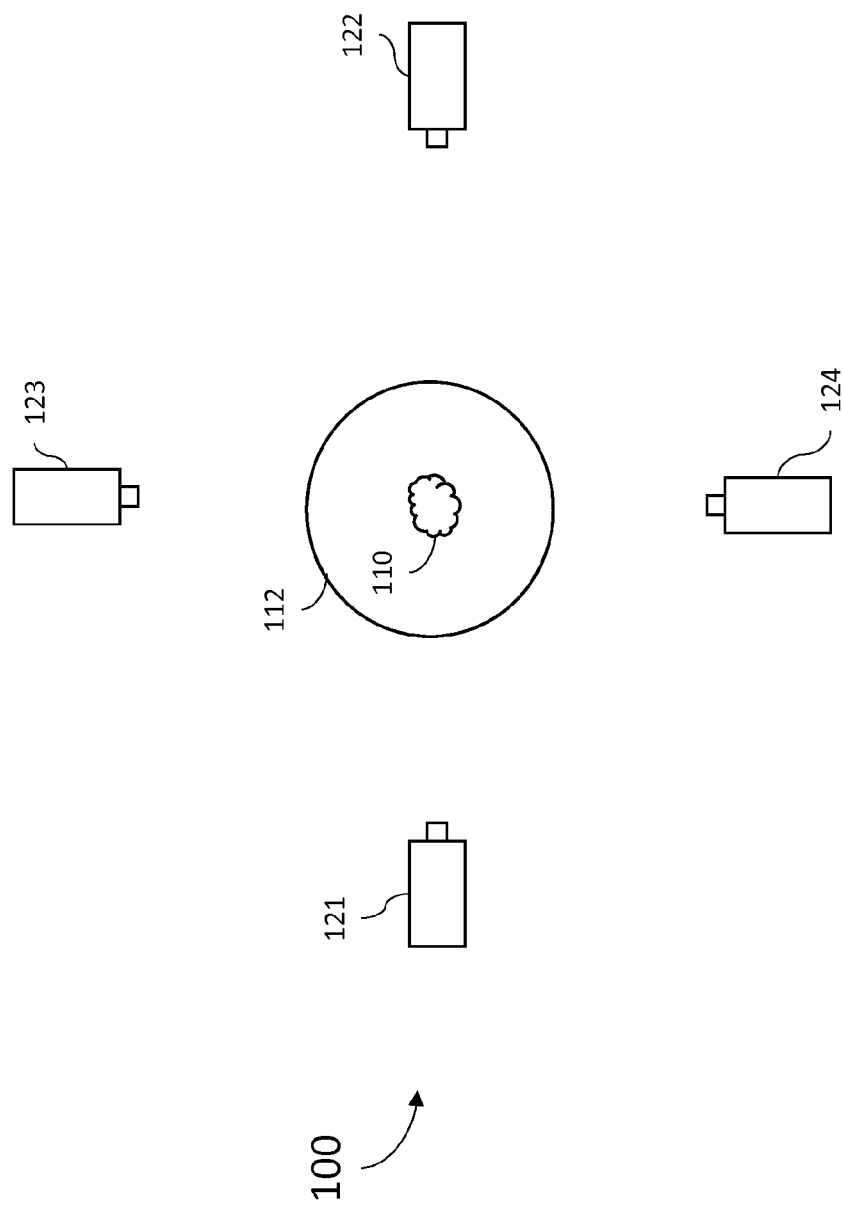

FIG. 1 is a simplified diagram illustrating operation of an optically dithered atomic inertial sensor 100 of one embodiment of the present disclosure. In the operation of such an atomic gyroscope, a sample of cold atoms (shown at 110) is created such as through laser cooling. This sample of cold atoms is referred to herein as a cold atom cloud 110. In some embodiments, the cold atom cloud 110 is maintained inside a vacuum chamber 112. The atoms of atom cloud 110 are typically alkali atoms and in some embodiments, cloud 110 may comprise rubidium or cesium atoms. In one embodiment, the laser cooling cools the atoms of cloud 110 down to a temperature of approximately 10 micro-Kelvin. Once cooled, the cold atom cloud 110 is released and allowed to fall under the influence of gravity in the manner shown in FIG. 2 and subjected to optical pulses from laser sources 121-124 to form an inertial sensor. Laser sources 121 and 122 are mutually aligned to apply a first set of laser beams along a first axis from opposing directions into cloud 110. Laser sources 123 and 124 are mutually aligned to apply a second set of laser beams along a second axis from opposing directions into cloud 110, where the second axis is orthogonal to the first axis. In alternate embodiments, any of the laser sources discussed here may be implementing using a distributed Bragg reflector (DBR), a vertical-cavity surface-emitting laser (VCSEL), or similar laser emitting devices. In some embodiments the laser sources may be laser producing devices themselves, or may simply output laser light directed to them from laser light generating devices (such as via beam splitters and/or mirrors, for example) with which they are in optical communication.

Figure 2:
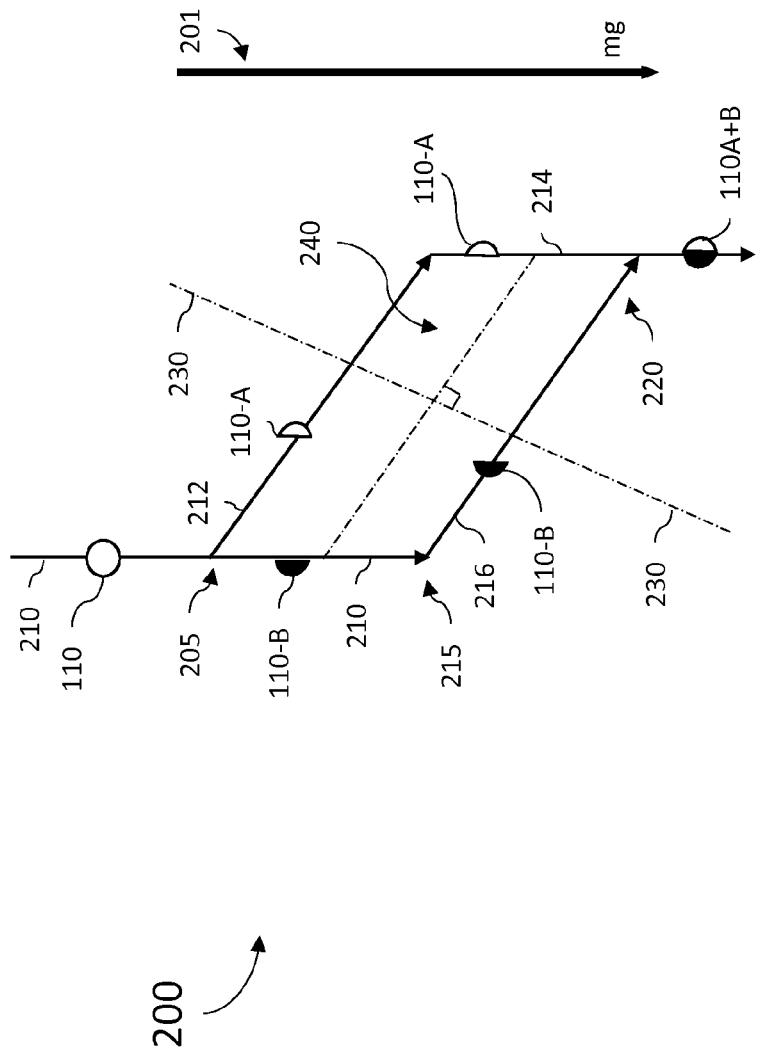

FIG. 2 is a diagram illustrating generally at 200 a rotation sense axis defined by the separation of the quantum-mechanical wave function of each of the atoms in atom cloud 110. As mentioned, the atoms of atom cloud 110 are permitted to fall under the influence of gravity (indicated by 201), such that the initial wave function for each of the atoms is following an original trajectory 210. In one embodiment, three pulses of light are applied by laser sources 121-124 onto cloud 110 to impart momentum to the atoms. A first optical pulse separates the initial quantum-mechanical wave function of each of the atoms in cloud 110 into 2 parts, shown in FIG. 2 as 110-A and 110-B. Application of the first pulse occurring at time to defines a point of separation 205. The first pulse imparts momentum onto a first half 110-A of each atom in the cloud 110 that causes half of its wave function to separate in space and travel a different trajectory from its other half 110-B. The departing trajectory travel by the first half 110-A is shown at 212. The second half 110-B of each atom's wave function, which did not receive a change in momentum from the first pulse, maintains travel along the original trajectory 210 of the initial wave function. As such, these two halves of the wave function become increasingly separated from each other in space as they travel. A second optical pulse reverses the momentum of each half of the wave function. Application of the second pulse is illustrated at 215 and occurs at some time period (τ1) after the first pulse at 205, when the two halves 110-A and 110-B will be at a predetermined distance from each other. The first half 110-A that separated from the original trajectory 210 of the wave function now shifts to a trajectory 214 that is parallel to the original trajectory 210 of the original wave function. For the second half 110-B that was not affected by the first pulse, the second pulse at 215 imparts momentum that causes it to deviate from the original trajectory 210, and follow a trajectory 216 that is parallel to the trajectory 212 traveled by the first half 110-A after the first pulse until both halves 110-A and 110-B intersect with each other at a recombination point 220.

At the recombination point 220, (occurs at some time period, τ2, after the second pulse) a third optical pulse is applied that imparts a momentum only on the second half 110-B, now causing it to shift to become aligned with the same trajectory 214 of the first half. That is, the third pulse recombines the two halves 110-A and 110-B of each atom's wave function such that the recombined atom now follows a path 214 that is parallel to that of the original trajectory 210, but spatially offset from the original trajectory. For the purpose of providing a reference of scale, in one embodiment, the atoms of the cloud 110 fall a few millimeters (e.g. about 5 mm) from first point 205 of wave function separation to the point 220 where the wave function is recombined. The horizontal offset in space of the final trajectory 214 from the original trajectory 210 is on the order of tens of microns. The small, planar area enclosed by the trajectories traveled by both halves of each atom, defines a parallelogram shaped sensing plane 240 having a rotational sense axis 230 that is perpendicular to the parallelogram shaped sensing plane 240. Accumulated phase differences in the recombined atoms (shown at 110A+B) due to rotation about the sense axis 230 can then be measured to determine a rotation rate. See, U.S. Patent Publication 2013/0213135 "Atom Interferometer with Adaptive Launch Direction and/or Position" and U.S. Patent Publication 2014/0022534 "Closed Loop Atomic Inertial Sensor" both of which are incorporated herein by reference in their entirety.

More specifically, alkali atoms, such as rubidium, have a single valence electron that is very sensitive to the laser pulses. That electron has a ground state with 2 hyperfine ground state possibilities (F=1 or F=2 for rubidium). Atoms within the atom cloud 110 are prepared to share the same initial ground state. When the atoms split and travel around the trajectories that define the parallelogram shaped sensing plane 240, rotation of the inertial sensor will cause the half of the wave function traveling along one path to pick up a different phase than the half traveling the other path. When the two halves are recombined at 220, they are recombined with the phase shift such that some portion of the recombined atoms 110A+B will shift from the first ground state (i.e., the original ground state they possessed prior to the second ground state, while the balance will retain the original ground state. The rotation rate about sense axis 230 can then be derived as a function of the number of atoms that retained the original ground state relative to the number that changes state. These measurements may be obtained, for example, through a fluorescence analysis by exposing the recombined atoms 110A+B to light of different frequencies. The frequency of light that causes fluorescence will indicate which ground state an atom possesses, and the relative responses of the sample to two different frequencies of light can thus be used to determine how many atoms are in each state.

Figure 3A:
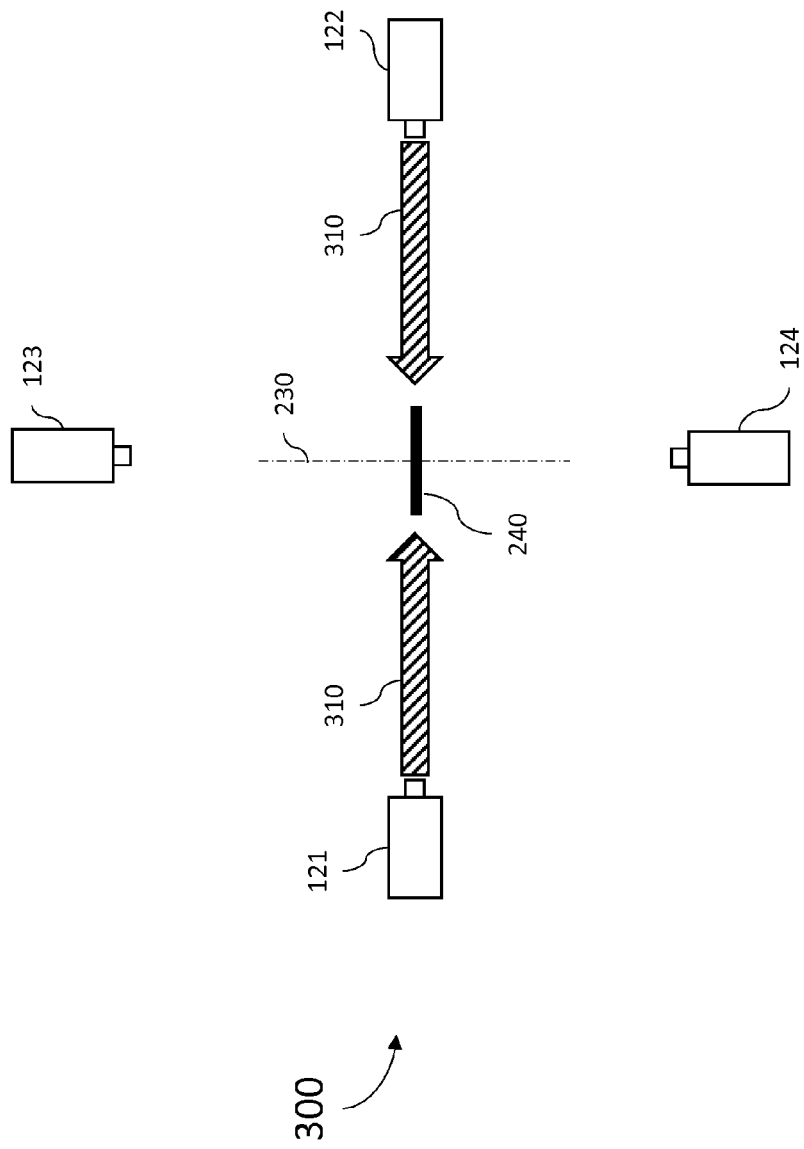
FIGS. 3A-3C are diagrams illustrating optical dithering of a rotation sense axis of one embodiment of the present disclosure.

Embodiments of the present disclosure introduce dithering to the sense axis 230 through either in-plane, out-of-plane rotation, or a combination of in-plane and out-of-plane rotation, of the parallelogram shaped sensing plane 240. FIG. 3A at 300 provides a top view of atom cloud 110, expanded into a parallelogram shaped plane 230 as discussed above, with the atoms of cloud 110 falling under the influence of gravity (or in some embodiments, under the combined influence of gravity and a laser induced force such as optical molasses, for example) down into to page. In FIG. 3A, a first set of mutually aligned lasers beams 310 (for example, from laser sources 121 and 122) is applied from opposing directions into cloud 110 to apply the three optical pulses discussed with respect to FIG. 2. Here, with just the single set of opposing laser beams 310 being applied, the area of the parallelogram shaped sensing plane 240 created by the pulses is aligned to the direction of the laser beams 310 so that the sense axis 230 forms along an axis orthogonal to the direction in which the laser beams 310 are applied.

Figure 3B:
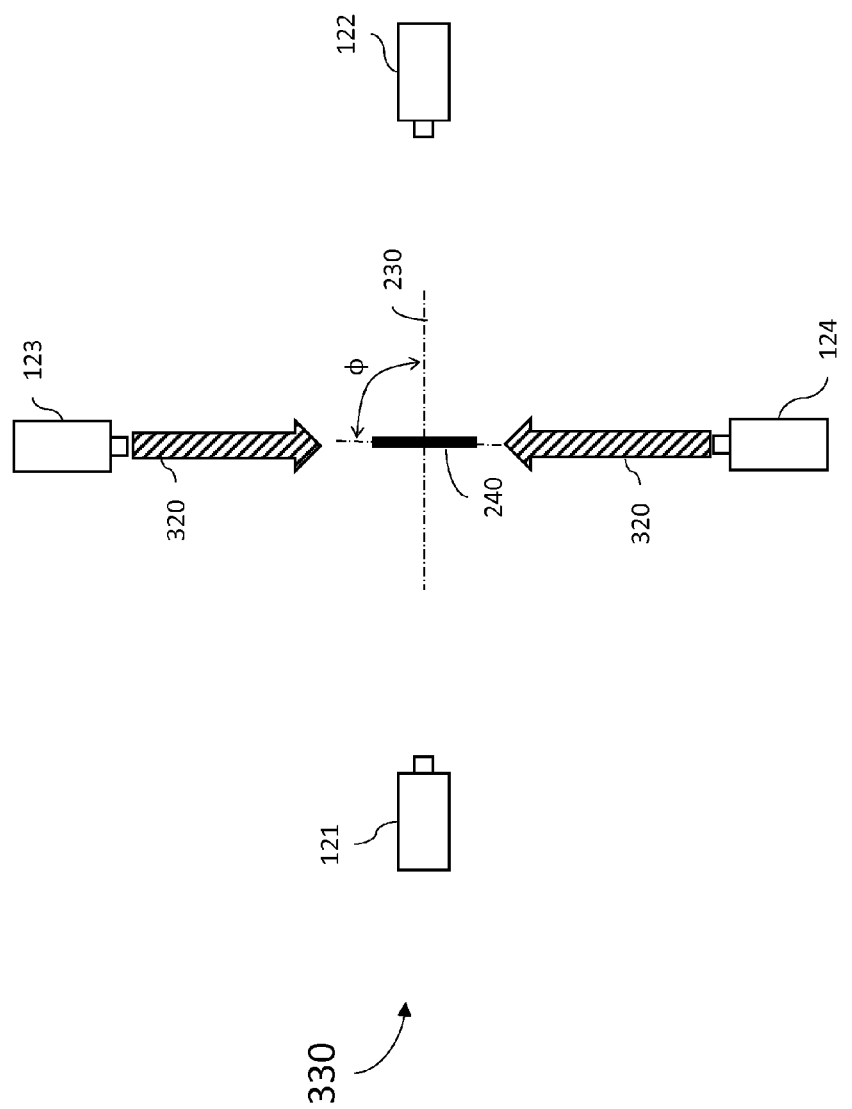

In FIG. 3B, a second set of mutually aligned laser beams 320 (for example, from laser sources 123 and 124) is applied in-plane and orthogonal to the first set of laser beams 310. With just the single set of opposing laser beams 320 being applied, the area of the parallelogram shaped sensing plane 240 created by the pulses is aligned to the direction of the laser beams 320 so that the sense axis 230 forms along an axis orthogonal to the direction in which the laser beams 320 are applied. In this way, the sense axis 230 has been rotated in-plane by an angle of $\phi=90°$ with respect to its position when just the first set of laser beams 310 was applied in FIG. 3A.

Figure 3C:
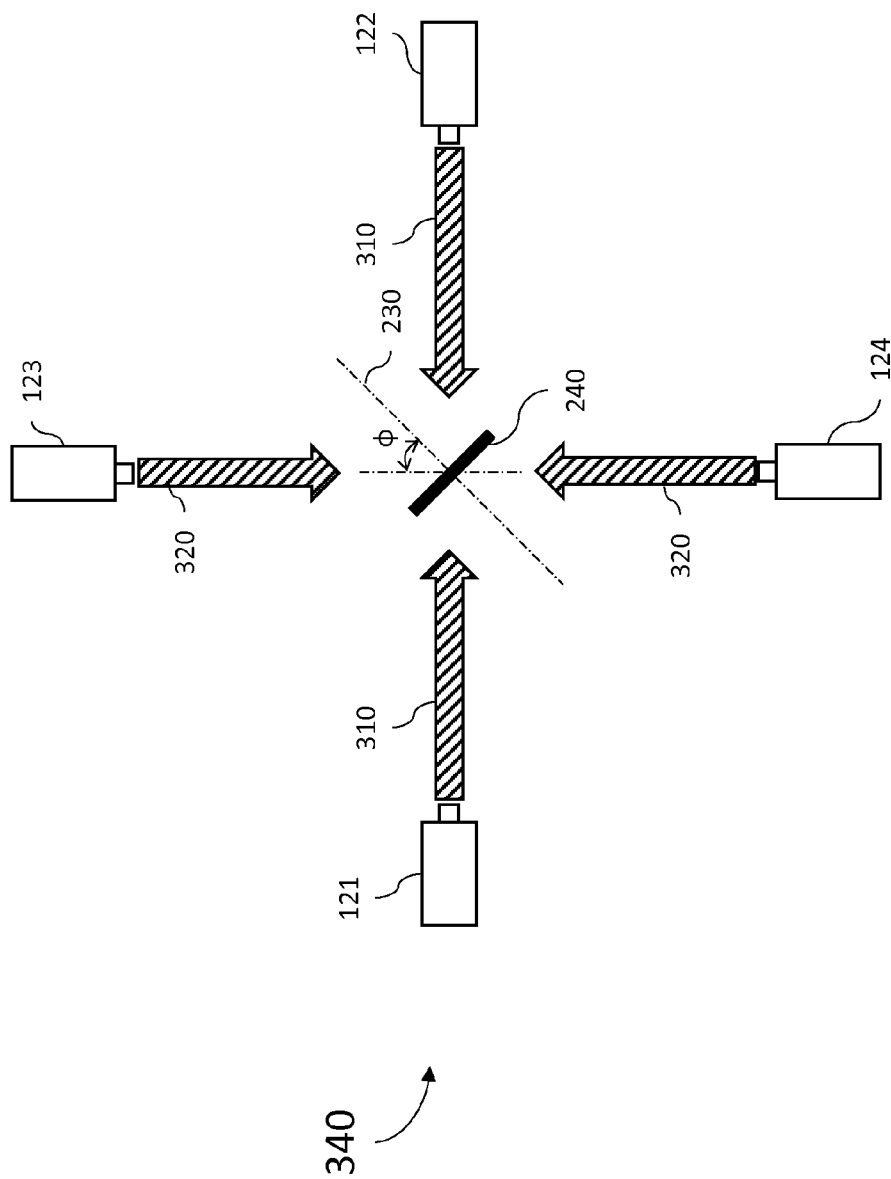

As shown in FIG. 3C, by simultaneously utilizing pulses from both sets 310 and 320 of laser beams to form the parallelogram shaped sensing plane 240, the sense axis 230 may be rotated to any arbitrary angle $\phi$. More specifically, by adjusting the relative magnitudes of the first set of laser beams 310 and the second set of laser beams 320, and pulsing the beams in a coherent fashion, dynamic in-plane rotation of the sense axis 230 can be achieved. In alternate implementations, the beams 310 and 320 may be derived from the same laser device, or otherwise phase locked so that the oscillating electric field that makes up beams 310 and 320 are oscillating coherently for both sets.

By shifting the relative magnitude of the first set of laser beams 310 with respect to the magnitude of the second set of laser beams 320, the sense axis 230 can be rotated to any angular position within the plane of FIGS. 3A-3C. With this configuration, gyroscopes can be realized that implement many different dithering schemes. For example, the sense axis 230 can be continuously rotated 360 degrees, or could be continuously switched between one axis location and another, or indexed between several different angular positions. In some embodiments, full 360 degree rotation is accomplished by swapping frequencies between opposing laser (i.e., facing) sources of a set as well. The direction of the Doppler shift determines the opening angle of the parallelogram.

The direction of the sense axis 230 at any point in time will follow a vector that is determined as a function of the direction and intensity of the laser beams. For example, where the first set of laser beams 310 are oriented orthogonally to the second set of laser beams 320, and are equal in magnitude to each other, the resulting sense axis 230 will be positioned along a vector having an angular displacement of $\phi=45°$ with respect to either of the beams. By reversing the frequency offset for one of the pair of lasers (for example, laser sources 121 and 122) the resulting sense axis 230 will be positioned along a vector having an angular displacement of $\phi=315°$. Reversing the frequency offset for one of the other pair of lasers (for example, laser sources 123 and 124) positions the sense axis 230 along a vector having an angular displacement of $\phi=135°$. Reversing the frequency offset for both pairs of laser sources positions the sense axis 230 along a vector having an angular displacement of $\phi=225°$. In one embodiment, the resulting angular displacement may be calculated through a basic vectorial summing of the direction and magnitudes of light for the two sets.

Figure 4:
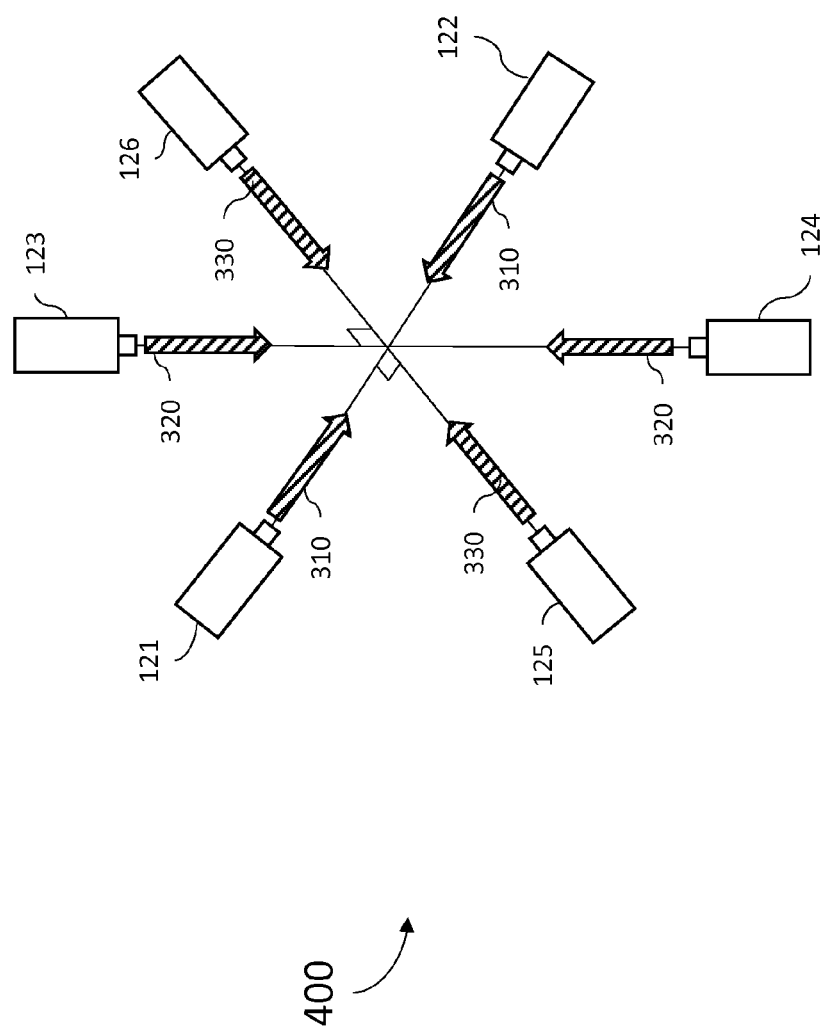
FIGS. 4 and 5 are diagrams illustrating an optically dithered atomic inertial sensor of one embodiment of the present disclosure.
Figure 5:
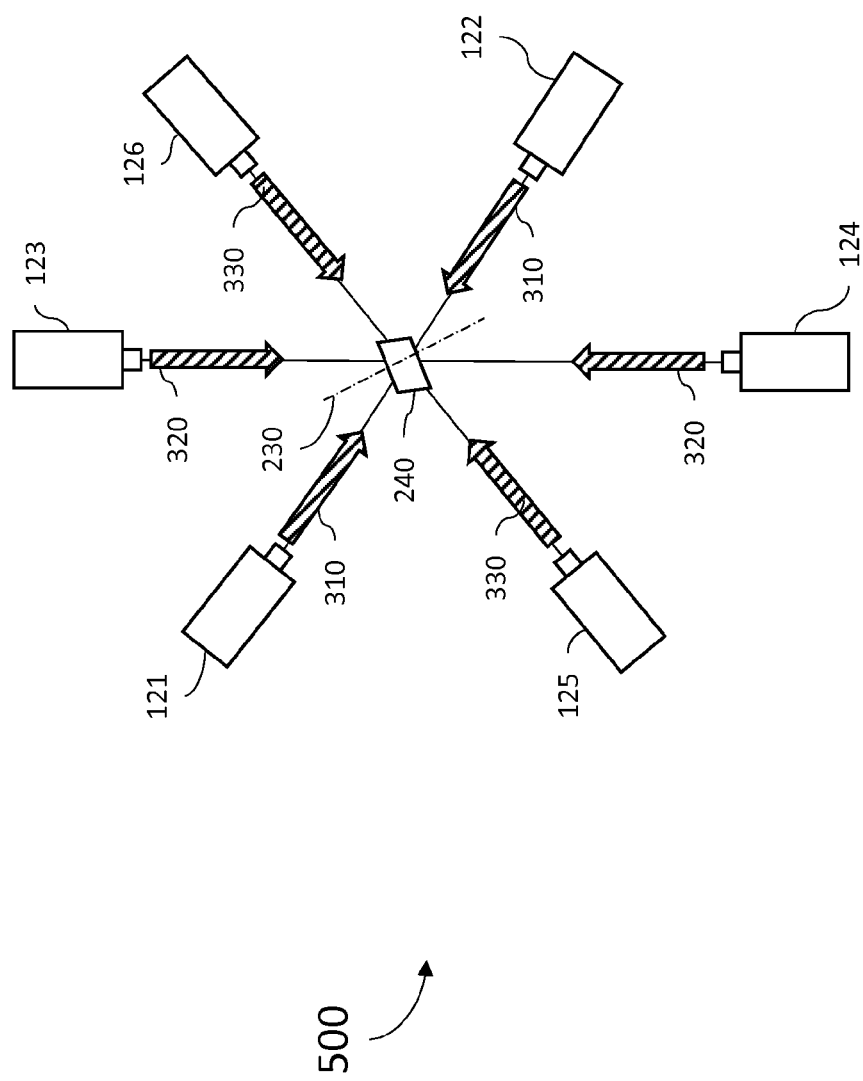

Thus with a single set of laser beams, the sense axis 230 is fixed in a direction orthogonal to the direction of the beams. By utilizing a second set of laser beams in a coherent fashion with the first set, the sense axis 230 may be rotated anywhere within the plane defined by the two sets of beams. As shown in FIGS. 4 and 5, by utilizing a third set of laser beams in a coherent fashion with the first and second sets, the sense axis 230 may further be rotated out of the plane defined by the first and second sets of beams to any position in three dimensional space. For example, FIG. 4 at 400 illustrates a third set of mutually aligned laser beams 330 (for example, from laser sources 125 and 126) which are applied in a direction mutually orthogonal to both the first set of laser beams 310 and the second set of laser beams 320. In alternate implementations, the beams 310, 320 and 330 may be derived from the same laser device, or otherwise phase locked so that the oscillating electric field that makes up beams 310, 320 and 330 are oscillating coherently for all sets. For such embodiments, as shown in FIG. 5 at 500, the direction of the sense axis 230 at any point in time will follow a vector that is determined as a function of the direction and intensity of all three sets of laser beams, and for some embodiments may be calculated through a vectorial summing of the direction and magnitudes of light for the three sets.

In some embodiments, controlling the magnitude of light in each of the sets of mutually aligned laser beams may be accomplished by controlling the output of the laser sources that generate each laser beam. In other embodiments, controlling the magnitude of light in each of the sets of mutually aligned laser beams may be accomplished through optical multiplexing of the laser lights that function as an atomic beam splitter and mirror. See, U.S. Patent Publication 2014/0016118 "MULTI-AXIS ATOMIC INERTIAL SENSOR SYSTEM" which is incorporated herein by reference in its entirety. For example, in one embodiment, a laser light beam from a laser source is split into two separate beams each directed onto atom cloud 110 as the first set 310 and the second set 320 of laser beams discussed above. The splitting may be controlled such that one of the resulting two separate beams has greater optical intensity than the other, so that the relative magnitude of the first set 310 and the second set 320 of laser beams may be manipulated to control the position of sense axis 230. In the same way, beam splitting may produce three separate beams each directed onto atom cloud 110 as beams 310, 320 and 330. In the same way, the splitting may be controlled such that the resulting three separate beams have differing optical intensities, so that the relative magnitude of the first set 310, the second set 320, and the third set 330 of laser beams may be manipulated to control the position of sense axis 230.

Although the different sets of laser beams used for pulsing and orienting the sense axis 230 are illustrated as being mutually orthogonal to each other, it should be noted that this only for the convenience of explanation. In other embodiments, different sets of laser beams used to position the sense axis 230 may be non-orthogonally aligned and still fall within the scope of the present disclosure. The principle of positioning the sense axis 230 remains the same and is based on vectorial summing of the direction and magnitudes of light from the laser beam sets.

For a miniature atomic gyroscope, dithering input axis 230 provides a boost in the signal to noise ratio of the rotation rate signal, which would decrease the time required for identifying the Earth's rotation axis. In some embodiment, an atomic inertial sensor such as discussed in any of the embodiments above also functions as a sensitive accelerometer which allows identification of the gravitation vertical axis, which is useful for both gyro-compassing and target location. In this case, optical dithering of sense axis 230 allows virtual leveling of an instrument, by mixing light from orthogonal axes in order to null any signal at the dither frequency. Field setup of a gyrocompass device utilizing embodiments described herein therefore could therefore be set up from a coarse initial alignment, followed by self-leveling (e.g., optical gimballing) of the instrument. For example, acceleration in the direction of gravity can be measured by applying the laser pulses from the top, parallel to the path of the falling atoms. The atom's wave function still spits similar to what is shown in FIG. 2, but the two paths are collinear so that the pulses merely cause changes in how rapidly each part of the wave function falls. That is, the first pulse causes ½ of each atom to gain momentum and fall more rapidly. The second pulse causes the first ½ to slow down and the second ½ to fall more rapidly. The third pulse recombines the two halves. In the same way as just described, a phase shift is imparted on the atoms which may be measured to determine acceleration.

Figure 6:
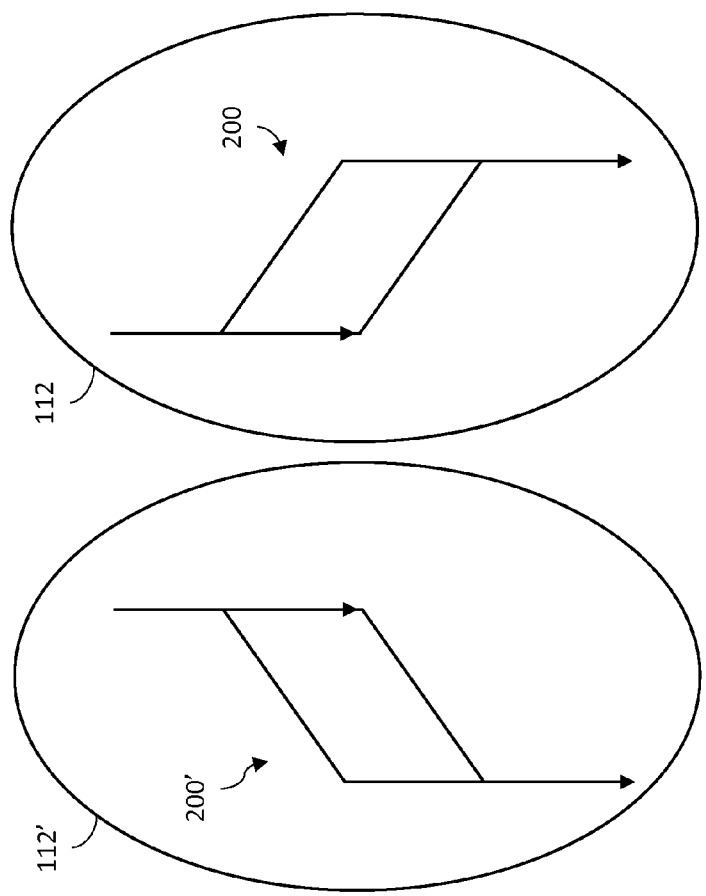
FIG. 6 is a diagram illustrating a device comprising a pair of optically dithered atomic inertial sensors of one embodiment of the present disclosure.

Although the atomic inertial sensors described in the present disclosure may sequence between functioning as a gyroscope and functioning as an accelerometer, in still other embodiments, such as shown in FIG. 6, a second vacuum chamber 102' having a second atom cloud formed into a parallelogram shaped sensing plane 240' is simultaneously operated side by side with the first vacuum chamber 102 that contains sensing plane 240, but configured to produce a parallelogram shaped sensing plane 240 opposite in orientation to the first. In this configuration, both sensors are configured to run as gyroscopes, but an addition phase shift will also accumulate in both sensors due to any acceleration. That is, the measurements are sensitive to both rotation and acceleration. This configuration measures rotation and acceleration, except when the gyroscope sense axis is parallel to gravity, which is the desired configuration brought about by the self-leveling procedure.

With the two operated sensors side-by-side (but mirrors of each other) the same acceleration can be measured from both of sensors, although the direction of rotation sensed by each will be opposite. This provides two equations and two unknowns so that rotation and acceleration data may be separated out as distinct measurements, in any arbitrary rotation in-plane or out-of-plane. The two sense axes within each of the vacuum chambers may then be dithered in the manner as described above.

Example Embodiments

Example 1 includes an optically dithered atomic inertial sensor, the inertial sensor comprising: a vacuum chamber containing an atom cloud of laser cooled alkali atoms, wherein the alkali atoms are free to fall under the influence of gravity; a first set of laser sources configured to apply a first set of laser beams into the atom cloud along a first axis; a second set of laser sources configured to apply a second set of laser beams into the atom cloud along a second axis; wherein the first set of laser beams and the second set of laser beams apply a series of coherent laser pulses into the atom cloud that separate a quantum-mechanical wave function of the alkali atoms along trajectories that define a sensing plane that is sensitive to rotation about a sensing axis oriented orthogonal to the sensing plane; and wherein the first set of laser sources and the second set of laser sources apply a dithering motion to the sensing axis by modulating a relative magnitude of the first set of laser beams with respect to the second set of laser beams.

Example 2 includes the inertial sensor of example 1, wherein the alkali atoms are free to fall under the combined influence of gravity and a laser induced force.

Example 3 includes the inertial sensor of any of examples 1-2, wherein the dithering motion comprises an in-plane dithering of the sensing axis.

Example 4 includes the inertial sensor of any of examples 1-3, further comprising: a third set of laser sources configured to apply a third set of laser beams into the atom cloud along a third axis; wherein the first set of laser beams, the second set of laser beams, and the third set of laser beams apply the series of coherent laser pulses into the atom cloud; and wherein the first set of laser sources, the second set of laser sources, and the third set of laser sources apply the dithering motion to the sensing axis by modulating relative magnitudes of the first set of laser beams, the second set of laser beams, and the third set of laser beams.

Example 5 includes the inertial sensor of example 4, wherein the first axis, the second axis, and the third axis are mutually orthogonal.

Example 6 includes the inertial sensor of any of examples 4-5, wherein the dithering motion comprises in-plane and out-of-plane dithering of the sensing axis.

Example 7 includes the inertial sensor of any of examples 1-6, wherein one or both of the first set of laser sources and the second set of laser sources comprise at least one laser producing device.

Example 8 includes the inertial sensor of any of examples 1-7, wherein one or both of the first set of laser sources and the second set of laser sources output laser light directed to them from a laser light generating device with which they are in optical communication.

Example 9 includes the inertial sensor of any of examples 1-8, wherein the first set of laser sources and the second set of laser sources are configured to modulate the relative magnitude of the first set of laser beams with respect to the second set of laser beams through optical multiplexing of laser light from a laser producing device.

Example 10 includes the inertial sensor of any of examples 1-9, further comprising: a second vacuum chamber containing a second atom cloud of laser cooled alkali atoms, wherein the alkali atoms are free to fall under the influence of gravity; wherein the first set of laser sources is further configured to apply the first set of laser beams into the second atom cloud along the first axis; wherein the second set of laser sources is further configured to apply the second set of laser beams into the second atom cloud along a second axis; wherein the first set of laser beams and the second set of laser beams apply a series of coherent laser pulses into the atom cloud that separate a quantum-mechanical wave function of the alkali atoms along trajectories that define a second sensing plane that is sensitive to rotation about a second sensing axis oriented orthogonal to the sensing plane; and wherein the first set of laser sources and the second set of laser sources apply a dithering motion to the second sensing axis by modulating the relative magnitude of the first set of laser beams with respect to the second set of laser beams.

Example 11 includes a method for optically dithering an atomic inertial sensor, the method comprising: applying a first set of laser beams along a first axis into an atom cloud of laser cooled alkali atoms, wherein the alkali atoms are free to fall under the influence of gravity within a vacuum chamber; applying a second set of laser beams along a second axis into the atom cloud of laser cooled alkali atoms, wherein the first set of laser beams and the second set of laser beams apply a series of coherent laser pulses into the atom cloud that separate a quantum-mechanical wave function of the alkali atoms along trajectories that define a sensing plane that is sensitive to rotation about a sensing axis oriented orthogonal to the sensing plane; and dithering the sensing axis by modulating a relative magnitude of the first set of laser beams with respect to the second set of laser beams.

Example 12 includes the method of example 11, wherein dithering the sensing axis comprises an in-plane dithering of the sensing axis.

Example 13 includes the method of any of examples 11-12, further comprising: apply a third set of laser beams into the atom cloud along a third axis, wherein the first set of laser beams, the second set of laser beams, and the third set of laser beams apply the series of coherent laser pulses into the atom cloud; and wherein dithering the sensing axis further comprising modulating relative magnitudes of the first set of laser beams, the second set of laser beams, and the third set of laser beams.

Example 14 includes the method of example 13, wherein dithering the sensing axis comprises in-plane and out-of-plane dithering of the sensing axis.

Example 15 includes the method of any of examples 11-14, wherein one or both of the first set of laser sources and the second set of laser sources comprise at least one laser producing device.

Example 16 includes the method of any of examples 11-15, wherein one or both of the first set of laser sources and the second set of laser sources output laser light directed to them from a laser light generating device with which they are in optical communication.

Example 17 includes the method of any of examples 11-16, wherein the first set of laser sources and the second set of laser sources are configured to modulate the relative magnitude of the first set of laser beams with respect to the second set of laser beams through optical multiplexing of laser light from a laser producing device.

Example 18 includes the method of any of examples 11-17, further comprising: applying the first set of laser beams along the first axis into a second atom cloud of laser cooled alkali atoms, wherein the alkali atoms are free to fall under the influence of gravity within a second vacuum chamber; applying the second set of laser beams along the second axis into the second atom cloud of laser cooled alkali atoms, wherein the first set of laser beams and the second set of laser beams apply a series of coherent laser pulses into the second atom cloud that separate a quantum-mechanical wave function of the alkali atoms along trajectories that define a second sensing plane that is sensitive to rotation about a second sensing axis oriented orthogonal to the second sensing plane; and dithering the second sensing axis by modulating the relative magnitude of the first set of laser beams with respect to the second set of laser beams.

Example 19 includes the method of any of examples 11-18, further comprising: performing a self-leveling by measuring a acceleration due to gravity; and adjusting the plane of dithering to be orthogonal to a gravity vector.

Example 20 includes the method of any of examples 11-19, further comprising: demodulating a dithered rotation output sensed along the sensing axis; and inferring an orientation of Earth's rotational vector with respect to the sensing axis.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

What is claimed is:

1. An optically dithered atomic inertial sensor, the inertial sensor comprising:

a vacuum chamber containing an atom cloud of laser cooled alkali atoms, wherein the alkali atoms are free to fall under the influence of gravity;

a first set of laser sources configured to apply a first set of laser beams into the atom cloud along a first axis;

a second set of laser sources configured to apply a second set of laser beams into the atom cloud along a second axis;

wherein the first set of laser beams and the second set of laser beams apply a series of coherent laser pulses into the atom cloud that separate a quantum-mechanical wave function of the alkali atoms along trajectories that define a sensing plane that is sensitive to rotation about a sensing axis oriented orthogonal to the sensing plane; and wherein the first set of laser sources and the second set of laser sources apply a dithering motion to the sensing axis by modulating a relative magnitude of the first set of laser beams with respect to the second set of laser beams.

2. The inertial sensor of claim 1, wherein the alkali atoms are free to fall under the combined influence of gravity and a laser induced force.

3. The inertial sensor of claim 1, wherein the dithering motion comprises an in-plane dithering of the sensing axis.

4. The inertial sensor of claim 1, further comprising:

a third set of laser sources configured to apply a third set of laser beams into the atom cloud along a third axis;

wherein the first set of laser beams, the second set of laser beams, and the third set of laser beams apply the series of coherent laser pulses into the atom cloud; and wherein the first set of laser sources, the second set of laser sources, and the third set of laser sources apply the dithering motion to the sensing axis by modulating relative magnitudes of the first set of laser beams, the second set of laser beams, and the third set of laser beams.

5. The inertial sensor of claim 4, wherein the first axis, the second axis, and the third axis are mutually orthogonal.

6. The inertial sensor of claim 4, wherein the dithering motion comprises in-plane and out-of-plane dithering of the sensing axis.

7. The inertial sensor of claim 1, wherein one or both of the first set of laser sources and the second set of laser sources comprise at least one laser producing device.

8. The inertial sensor of claim 1, wherein one or both of the first set of laser sources and the second set of laser sources output laser light directed to them from a laser light generating device with which they are in optical communication.

9. The inertial sensor of claim 1, wherein the first set of laser sources and the second set of laser sources are configured to modulate the relative magnitude of the first set of laser beams with respect to the second set of laser beams through optical multiplexing of laser light from a laser producing device.

10. The inertial sensor of claim 1, further comprising:

a second vacuum chamber containing a second atom cloud of laser cooled alkali atoms, wherein the alkali atoms are free to fall under the influence of gravity;

wherein the first set of laser sources is further configured to apply the first set of laser beams into the second atom cloud along the first axis;

wherein the second set of laser sources is further configured to apply the second set of laser beams into the second atom cloud along a second axis;

wherein the first set of laser beams and the second set of laser beams apply a series of coherent laser pulses into the atom cloud that separate a quantum-mechanical wave function of the alkali atoms along trajectories that define a second sensing plane that is sensitive to rotation about a second sensing axis oriented orthogonal to the sensing plane; and wherein the first set of laser sources and the second set of laser sources apply a dithering motion to the second sensing axis by modulating the relative magnitude of the first set of laser beams with respect to the second set of laser beams.

11. A method for optically dithering an atomic inertial sensor, the method comprising:

applying a first set of laser beams along a first axis into an atom cloud of laser cooled alkali atoms, wherein the alkali atoms are free to fall under the influence of gravity within a vacuum chamber;

applying a second set of laser beams along a second axis into the atom cloud of laser cooled alkali atoms, wherein the first set of laser beams and the second set of laser beams apply a series of coherent laser pulses into the atom cloud that separate a quantum-mechanical wave function of the alkali atoms along trajectories that define a sensing plane that is sensitive to rotation about a sensing axis oriented orthogonal to the sensing plane; and dithering the sensing axis by modulating a relative magnitude of the first set of laser beams with respect to the second set of laser beams.

12. The method of claim 11, wherein dithering the sensing axis comprises an in-plane dithering of the sensing axis.

13. The method of claim 11, further comprising:

apply a third set of laser beams into the atom cloud along a third axis, wherein the first set of laser beams, the second set of laser beams, and the third set of laser beams apply the series of coherent laser pulses into the atom cloud; and wherein dithering the sensing axis further comprising modulating relative magnitudes of the first set of laser beams, the second set of laser beams, and the third set of laser beams.

14. The method of claim 13, wherein dithering the sensing axis comprises in-plane and out-of-plane dithering of the sensing axis.

15. The method of claim 11, wherein one or both of the first set of laser sources and the second set of laser sources comprise at least one laser producing device.

16. The method of claim 11, wherein one or both of the first set of laser sources and the second set of laser sources output laser light directed to them from a laser light generating device with which they are in optical communication.

17. The method of claim 11, wherein the first set of laser sources and the second set of laser sources are configured to modulate the relative magnitude of the first set of laser beams with respect to the second set of laser beams through optical multiplexing of laser light from a laser producing device.

18. The method of claim 11, further comprising:

applying the first set of laser beams along the first axis into a second atom cloud of laser cooled alkali atoms, wherein the alkali atoms are free to fall under the influence of gravity within a second vacuum chamber;

applying the second set of laser beams along the second axis into the second atom cloud of laser cooled alkali atoms, wherein the first set of laser beams and the second set of laser beams apply a series of coherent laser pulses into the second atom cloud that separate a quantum-mechanical wave function of the alkali atoms along trajectories that define a second sensing plane that is sensitive to rotation about a second sensing axis oriented orthogonal to the second sensing plane; and dithering the second sensing axis by modulating the relative magnitude of the first set of laser beams with respect to the second set of laser beams.

19. The method of claim 11, further comprising:

performing a self-leveling by measuring a acceleration due to gravity; and adjusting the plane of dithering to be orthogonal to a gravity vector.

20. The method of claim 11, further comprising:

demodulating a dithered rotation output sensed along the sensing axis; and inferring an orientation of Earth's rotational vector with respect to the sensing axis.

* * * * *